US012653939B2

(12) United States Patent
Wei

(10) Patent No.: US 12,653,939 B2
(45) Date of Patent: Jun. 16, 2026

(54) ELECTRIC NASAL ASPIRATOR WITH ANTI-BLOCKING AND CLEANING FUNCTIONS

(71) Applicant: Shenzhen Dongjiang Technology Co., LTD, Shenzhen (CN)

(72) Inventor: Jun Jie Wei, Gongyi (CN)

(73) Assignee: SHENZHEN DONGJIANG TECHNOLOGY CO., LTD, Shenzhen (CN)

( * ) Notice: Subject to any disclaimer, the term of this patent is extended or adjusted under 35 U.S.C. 154(b) by 310 days.

(21) Appl. No.: 18/520,633

(22) Filed: Nov. 28, 2023

(65) Prior Publication Data

US 2024/0091427 A1 Mar. 21, 2024

(30) Foreign Application Priority Data

Oct. 20, 2023 (CN) .......................... 202322843366.2

(51) Int. Cl.
*A61M 1/00* (2006.01)
(52) U.S. Cl.
CPC ................. *A61M 1/65* (2021.05); *A61M 1/64* (2021.05); *A61M 1/71* (2021.05); *A61M 1/74* (2021.05); *A61M 2205/502* (2013.01); *A61M 2205/8206* (2013.01); *A61M 2205/8256* (2013.01); *A61M 2210/0618* (2013.01)

(58) Field of Classification Search
CPC ............ A61M 1/64; A61M 1/71; A61M 1/74; A61M 2205/502; A61M 2205/8256; A61M 2210/0618
See application file for complete search history.

(56) References Cited

U.S. PATENT DOCUMENTS

2012/0029486 A1 2/2012 Laerdal et al.
2014/0296793 A1 10/2014 Varney et al.
2016/0263295 A1 9/2016 Mehta et al.
2022/0143294 A1* 5/2022 Wei ......................... A61M 1/64

FOREIGN PATENT DOCUMENTS

CN 221206299 U * 6/2024

* cited by examiner

*Primary Examiner* — Leslie R Deak
(74) *Attorney, Agent, or Firm* — Hemisphere Law, PLLC

(57) ABSTRACT

The present disclosure discloses an electric nasal aspirator with anti-blocking and cleaning functions, including a housing assembly, provided with an exhaust hole and an air suction column penetrating through the housing assembly; a circuit board, fixedly arranged in the housing assembly; a collection cup assembly, detachably arranged on the housing assembly, wherein the collection cup assembly includes an outer cover, a collection cup, and a suction nozzle; the outer cover is detachably hermetically connected to the housing assembly; the collection cup includes a connecting column and a collection chamber; the connecting column is hollowly tubular and detachably arranged on the air suction column.

17 Claims, 11 Drawing Sheets

ELECTRIC NASAL ASPIRATOR WITH ANTI-BLOCKING AND CLEANING FUNCTIONS

TECHNICAL FIELD

The present disclosure relates to the technical field of nasal aspirators, and particularly, to an electric nasal aspirator with anti-blocking and cleaning functions.

BACKGROUND

Children having a cold and stuffy nose are unable to blow their own noses. A stuff nose makes a child have difficulty in breathing and cry, and even affects the sleep of the child. A nasal aspirator can help parents to remove secretions from the nasal cavity of a child to make the child breathe smoothly. It is hard for the parents to use a traditional manual nasal aspirator to extract the secretions from the nasal cavity of the child. Moreover, the parents are unable to control a force of using the traditional manual nasal aspirator, so it is easy to injure the nasal cavity of the child. An existing automatic nasal aspirator usually includes a suction head and a main body portion; the main body portion is provided with an air pump which generates a negative pressure to suck the nasal mucus out of the nasal cavities of children. However, when the existing nasal aspirator works, dirt is sucked into the host portion and can easily block an air suction port, and the dirt is then sucked into the air pump of the host portion. As the interior of the air pump cannot be cleaned, a large number of bacteria and odors can grow, and a user may be infected with bacteria again. Therefore, an electric nasal aspirator with anti-blocking and cleaning functions is provided to solve the problems of the existing nasal aspirator that the air suction port is easily blocked and is inconvenient to clean.

SUMMARY

One objective of the present disclosure is to provide an electric nasal aspirator with anti-blocking and cleaning functions, so as to solve the problems of the existing nasal aspirator that the air suction port is easily blocked and is inconvenient to clean.

An electric nasal aspirator with the anti-blocking and cleaning functions of the present disclosure can be implemented by the following technical solutions:

The present disclosure discloses an electric nasal aspirator with anti-blocking and cleaning functions, including a housing assembly, which is a hollow chamber, wherein the housing assembly is provided with an exhaust hole and an air suction column penetrating through the housing assembly; a circuit board, fixedly arranged in the housing assembly; a collection cup assembly, detachably arranged on the housing assembly, wherein the collection cup assembly includes an outer cover, a collection cup, and a suction nozzle; the outer cover is detachably hermetically connected to the housing assembly; the collection cup includes a connecting column and a collection chamber; the connecting column is hollowly tubular and detachably arranged on the air suction column; an upper end of the connecting column is provided with at least one air suction hole penetrating through the upper end; the air suction column is communicated to a hollow chamber encircled by the outer cover and the housing assembly; the collection chamber is fixedly arranged on the connecting column and can closely abut against an inner wall of the outer cover; at least one air suction slot body penetrating through a side edge of the collection chamber is arranged on the side edge, and the outer cover is communicated to the suction nozzle through the at least one air suction slot body; the suction nozzle is detachably connected to the outer cover and extends into the collection cup; the nasal mucus is directly collected and stored in the collection cup through the suction nozzle; an air pump assembly, configured to provide a negative pressure suction force for the collection cup assembly, wherein the air pump assembly is hermetically communicated to the air suction column and the exhaust hole and is electrically connected to the circuit board; a button assembly, fixedly arranged on the circuit board and penetrating through the housing assembly, wherein the button assembly controls on/off and function settings of the nasal aspirator; and a battery assembly, fixedly arranged in the housing assembly and configured to provide electric energy for the circuit board, the air pump assembly, and the button assembly.

Preferably, the air pump assembly includes an air pump main body, an exhaust pipe, and an air suction pipe; the air pump main body is arranged in the housing assembly; two ends of the exhaust pipe are respectively hermetically communicated with an exhaust end of the air pump main body and the exhaust hole; and two ends of the air suction pipe are respectively hermetically communicated with an air suction end of the air pump main body and the air suction column.

Preferably, the housing assembly includes a main housing and a cup holder; the main housing is a hollow chamber with a slope; the cup holder is fixedly arranged on the main housing; and a joint between the main housing and the cup holder is welded ultrasonically to improve the waterproof performance of both the main housing and the cup holder.

Preferably, at least one clamping slot is arranged on an outer side of the cup holder; at least one buckle is arranged on the inner wall of the outer cover; and the at least one buckle is matched with the corresponding clamping slot, so that the outer cover is detachably and fixedly connected to the cup holder.

Preferably, a sealing ring is arranged at a joint between the outer cover and the cup holder; and the sealing ring improves the sealing performance of both the outer cover and the cup holder.

Preferably, the outer cover is provided with an external thread; an inner wall of the suction nozzle is provided with an internal thread; and the suction nozzle is in detachably threaded connection to the outer cover through cooperation between the internal thread and the external thread.

Preferably, the connecting column and the collection chamber are integrally formed, facilitating processing of the connecting column and the collection chamber; and a material of the connecting column and a material of the collection chamber are silica gel, so that the collection chamber closely abuts against the inner wall of the outer cover.

Preferably, the suction nozzle includes a suction nozzle main body and a suction nozzle channel; the suction nozzle main body is in detachably threaded connection to the outer cover; a front end of the suction nozzle main body is provided with a suction nozzle port penetrating through the front end; and the suction nozzle channel is arranged in the suction nozzle main body in a penetrating manner and extends into the collection chamber.

Preferably, the suction nozzle port is a funnel-shaped incision suction nozzle port, a straight head suction nozzle port, or a round head suction nozzle port, and the corresponding suction nozzle port is adapted according to an actual need.

Preferably, a material of the suction nozzle is food grade silica gel.

Preferably, when the battery assembly is a rechargeable battery, a charging assembly is arranged in the housing assembly; and the charging assembly penetrates through the housing assembly and is electrically connected to the circuit board.

Preferably, the charging assembly includes a connecting circuit board and a charging interface; the connecting circuit board is fixedly arranged in the housing assembly and electrically connected to the circuit board; the charging interface is fixedly arranged on the connecting circuit board and penetrates through the housing assembly; the battery assembly is charged through the charging interface; the charging interface is movably provided with a protective plug; and the protective plug prevents foreign matters from entering the charging interface.

Preferably, the charging interface adopts a Micro USB interface, a Type-C interface, or a Lightning interface.

Preferably, the electric nasal aspirator with the anti-blocking and cleaning functions further includes a display assembly, wherein the display assembly is fixedly arranged on the circuit board and penetrates through the housing assembly and is configured to perform real-time displaying; and the display assembly adopts a digital tube, a liquid crystal display (LCD) screen, or a light-emitting diode (LED) display screen.

Preferably, the electric nasal aspirator with the anti-blocking and cleaning functions further includes an LED lamp and a speaker, wherein the LED lamp and the speaker are respectively fixedly arranged in the housing assembly; light emitted by the LED lamp can be transmitted out of the housing assembly and the collection cup assembly in sequence to attract attention of a child through the LED lamp and the speaker and relieve discomfort in a nasal mucus process of the child.

Preferably, the button assembly includes an on/off button, an audio button, a light button, and a function setting button; the nasal aspirator is switched on or off through the on/off button; the speaker and the LED lamp are controlled to work respectively through the audio button and the light button; and functions are switched and set through the function setting button.

Preferably, the LED lamp can be changed in multiple colors and can flicker to achieve functions of creating different atmospheres to attract the attention of the child and relieving the discomfort in the nasal mucus process of the child.

Compared with the prior art, the electric nasal aspirator with the anti-blocking and cleaning functions of the present disclosure has the beneficial effects below:

According to the electric nasal aspirator with the anti-blocking and cleaning functions of the present disclosure, since the air suction hole and the air suction slot body are arranged on the connecting column and the collection chamber respectively, the suction nozzle, the collection chamber, the air suction slot body, the outer cover, the air suction hole, the connecting column, the air suction column, the air pump assembly, and the exhaust hole communicated to each other in sequence to form an air suction channel. A negative pressure causes the suction nozzle to suck the nasal mucus in the nasal cavity into the collection chamber. Due to the close abutment between the collection chamber and the inner wall of the outer cover, it is difficult for the nasal mucus in the collection chamber to flow into a sealed chamber formed by the outer cover and a nasal aspirator main body. The nasal mucus in the collection chamber will overflow into the sealed chamber if the amount of the nasal mucus exceeds a capacity of the collection chamber, and the air suction hole on the connecting column will guide a source air hole that generating a negative pressure to a middle position of the connecting column. This design makes it also difficult for the nasal mucus that overflows into the sealed chamber to enter the nasal aspirator main body through the air suction column, thereby avoiding damage to the circuit board and the air pump in the nasal aspirator main body and effectively solving the problem of the existing nasal aspirator that the air suction port is easily blocked.

The detachable connection between the outer cover, the collection cup, and the suction nozzle in the electric nasal aspirator with the anti-blocking and cleaning functions facilitates performing cleaning and disinfection operations on the three components. When the air pump main body needs to be cleaned, cleaning water enters the air pump main body through the air suction column to clean the interior of the air pump main body and then is discharged from the exhaust hole. As the air pump assembly is hermetically communicated to the exhaust hole and the air suction column, the cleaning water will not enter the housing assembly, thereby effectively preventing damage to components arranged inside the housing assembly and effectively solving the problem of inconvenient cleaning of the existing nasal aspirator.

BRIEF DESCRIPTION OF THE DRAWINGS

For clearer descriptions of the technical solutions of the embodiments of the present disclosure, the accompanying drawings required to be used in the embodiments are briefly introduced below. It should be understood that the accompanying drawings below are only some embodiments of the present disclosure. Therefore, the embodiments shall not be regarded as limitations on the scope. A person of ordinary skill in the art can also derive other relevant drawings according to these drawings without creative work.

Figure 1:
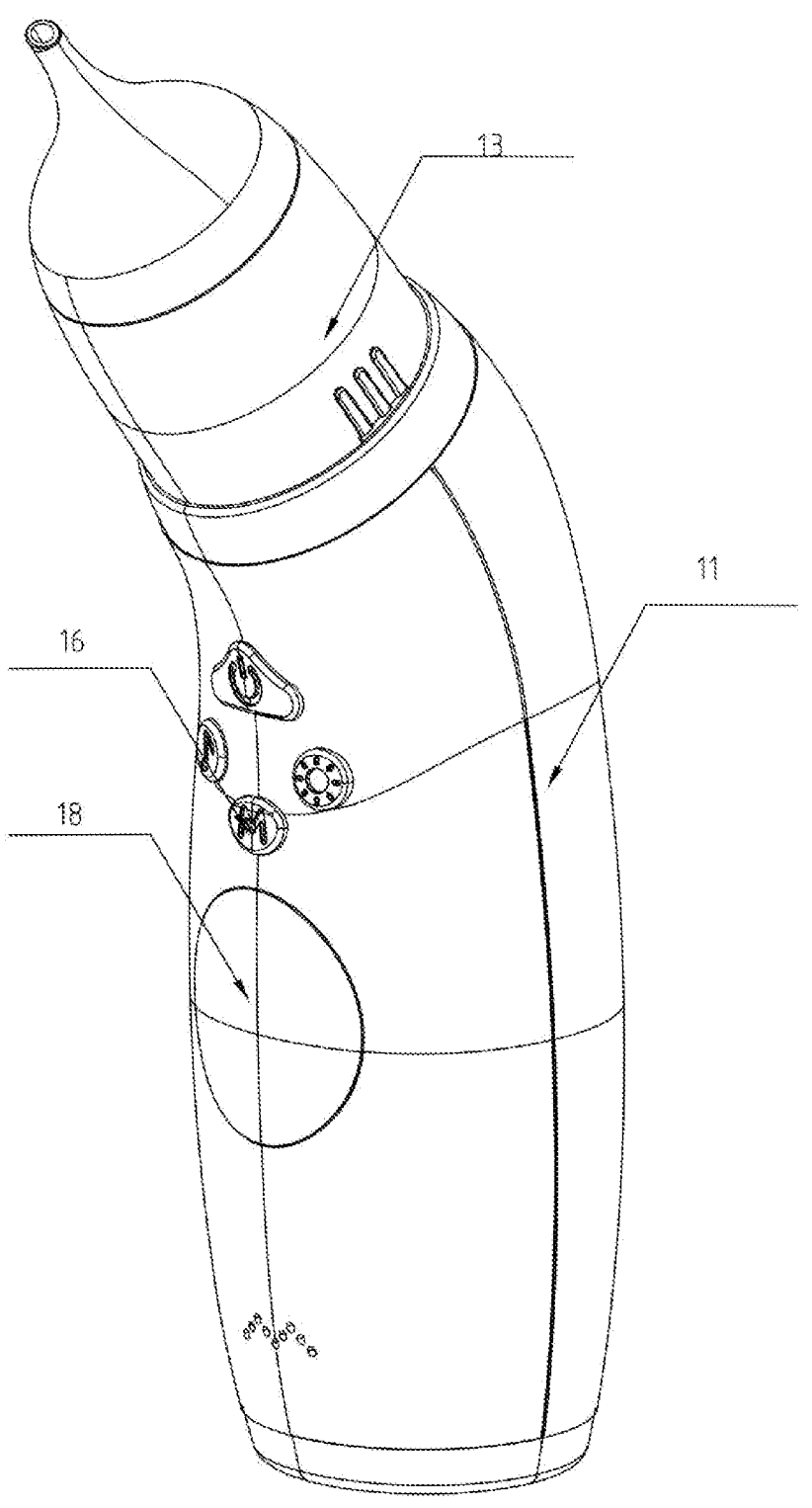
FIG. 1 is a schematic structural diagram of an electric nasal aspirator with anti-blocking and cleaning functions according to the present disclosure.
Figure 2:
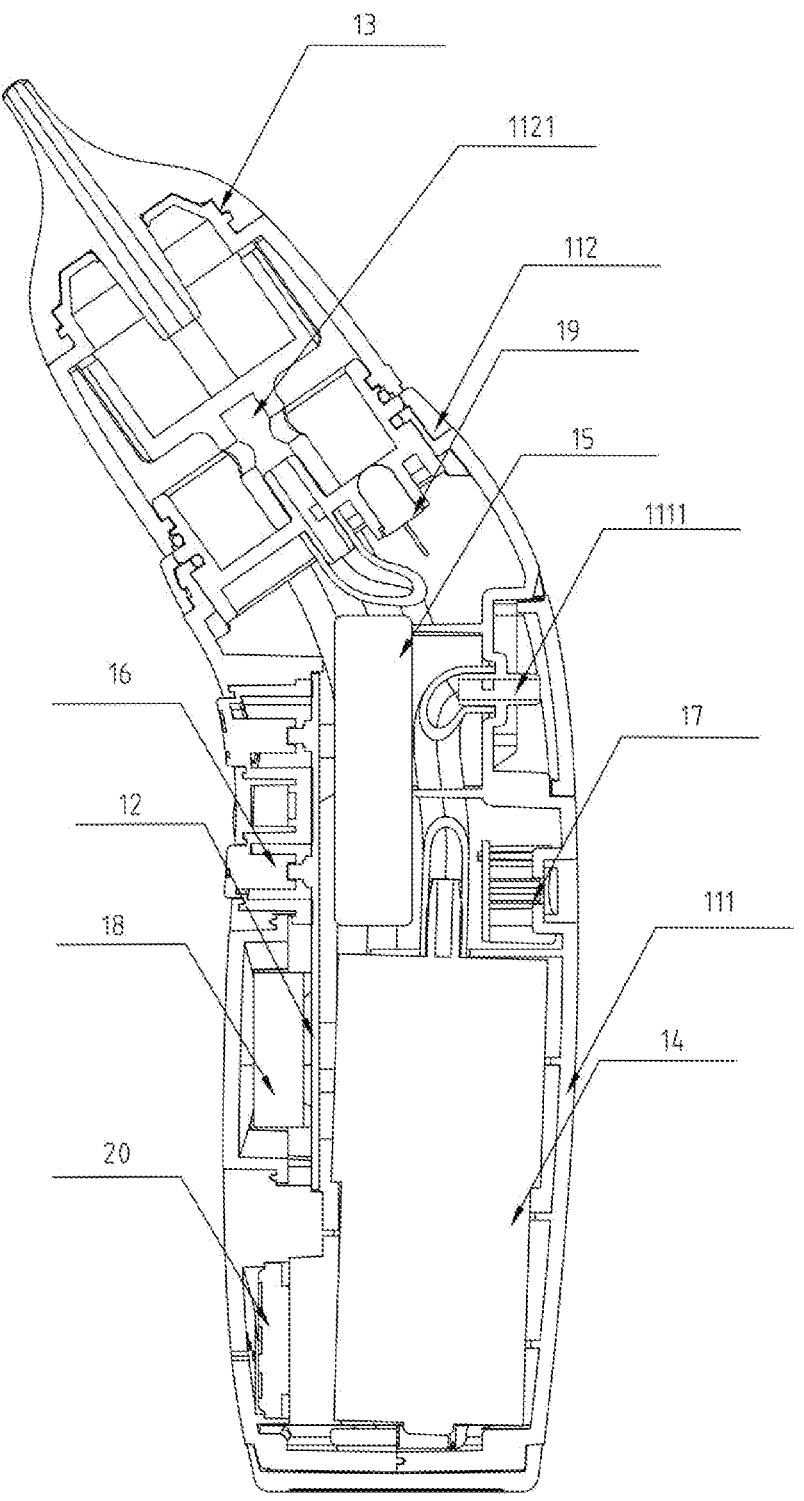
FIG. 2 is a structural sectional view of the electric nasal aspirator with the anti-blocking and cleaning functions shown in FIG. 1 according to the present disclosure.

Numerals in the drawings: 11: housing assembly; 111: main housing; 1111: exhaust hole; 11111: exhaust cover; 1112: first through hole; 1113: charging interface; 1114: speaker hole; 112: cup holder; 1121: air suction column; 1122: clamping slot; 1123: sealing ring; 12: circuit board; 13: collection cup assembly; 131: outer cover; 1311: second through hole; 1312: external thread; 1313: buckle; 1314: cover twisting member; 132: collection cup; 1321: connecting column; 13211: air suction hole; 1322: collection chamber; 13221: air suction slot body; 133: suction nozzle; 1331: suction nozzle main body; 13311: funnel-shaped incision suction nozzle port; 13312: straight head suction nozzle port; 13313: round head suction nozzle port; 1332: suction nozzle channel; 14: air pump assembly; 141: air pump main body; 142: exhaust pipe; 143: air suction pipe; 15: battery assembly; 16: button assembly; 17: charging assembly; 171: connecting circuit board; 172: charging interface; 1721: protective plug; 18: display assembly; 19: LED lamp; and 20: speaker.

DETAILED DESCRIPTION OF THE EMBODIMENTS

In order to make the objectives, technical solutions, and advantages of the embodiments of the present disclosure clearer, the technical solutions in the embodiments of the present disclosure are clearly described below with reference to the accompanying drawings in the embodiments of the present disclosure. Apparently, the described embodiments are merely some rather than all of the embodiments of the present disclosure. Assemblies of the embodiments of the present disclosure commonly described and shown in the accompanying drawings here may be arranged and designed in a variety of different configurations.

Therefore, the following detailed descriptions of the embodiments of the present disclosure provided in the accompanying drawings are not intended to limit the scope of the claimed present disclosure, but merely represents selected embodiments of the present disclosure. All other embodiments obtained by a person of ordinary skill in the art based on the embodiments of present disclosure without making creative efforts shall fall within the protection scope of present disclosure.

It should be noted that similar reference numerals and letters indicate similar items in the following drawings. Therefore, once a certain item is defined in one drawing, it is unnecessary to further define and explain it in the subsequent drawings.

Referring to FIG. 1 to FIG. 5, an electric nasal aspirator with anti-blocking and cleaning functions of the present disclosure mainly includes a housing assembly 11, a circuit board 12, a collection cup assembly 13, an air pump assembly 14, a battery assembly 15, a button assembly 16, a charging assembly 17, a display assembly 18, an LED lamp 19, and a speaker 20. The housing assembly 11 is a hollow chamber and is provided with an exhaust hole 1111 and an air suction column 1121 penetrating through the housing assembly. The circuit board 12, the battery assembly 15, the air pump assembly 14, the LED lamp 19, and the speaker 20 are respectively fixedly arranged in the housing assembly 11. The circuit board 12 is electrically connected to the air pump assembly 14, the battery assembly 15, the button assembly 16, the charging assembly 17, the display assembly 18, the LED lamp 19, and the speaker 20, respectively. One end of the air pump assembly 14 is hermetically communicated to the air suction column 1121, and the other end is hermetically communicated to the exhaust hole 1111, so as to provide a negative pressure suction force for the collection cup assembly 13. The battery assembly 15 provides power for the circuit board 12, the air pump assembly 14, the button assembly 16, the display assembly 18, the LED lamp 19, and the speaker 20, respectively. Light emitted by the LED lamp 19 can be transmitted out of the housing assembly 11 and the collection cup assembly 13 in sequence, and the speaker 20 can play audio information. The function of the LED lamp 19 and the function of the speaker 20 are to attract the attention of a child and relieve discomfort in a nasal mucus suction process of the child. The collection cup assembly 13 is detachably arranged on the housing assembly 11, and the nasal mucus is collected and stored through the collection cup assembly 13. The button assembly 16 and the display assembly 18 are fixedly arranged on the circuit board 12 and penetrate through the housing assembly 11. On/off and function settings of the nasal aspirator are controlled by the button assembly 16, and a function of the display assembly 18 is to perform real-time displaying. The charging assembly 17 is fixedly arranged in the housing assembly 11 and penetrates through the housing assembly 11, and has a function of charging the battery assembly 15.

Referring to FIG. 1 to FIG. 5, in this embodiment, the housing assembly 11 includes a main housing 111 and a cup holder 112; the main housing 111 is a hollow chamber with a slope; and the cup holder 112 is fixedly arranged on the main housing 111. In order to improve the waterproof performance of both the main housing 111 and the cup holder 112, a joint between the main housing 111 and the cup holder 112 is welded ultrasonically to prevent cleaning water from permeating into the main housing 111 from the joint between the main housing and the cup holder during cleaning of the nasal aspirator.

Figure 3:
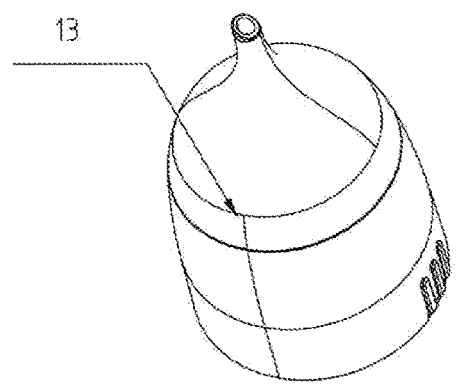
FIG. 3 is a schematic diagram of a partially exploded structure of the electric nasal aspirator with the anti-blocking and cleaning functions shown in FIG. 1 according to the present disclosure.
Figure 3:
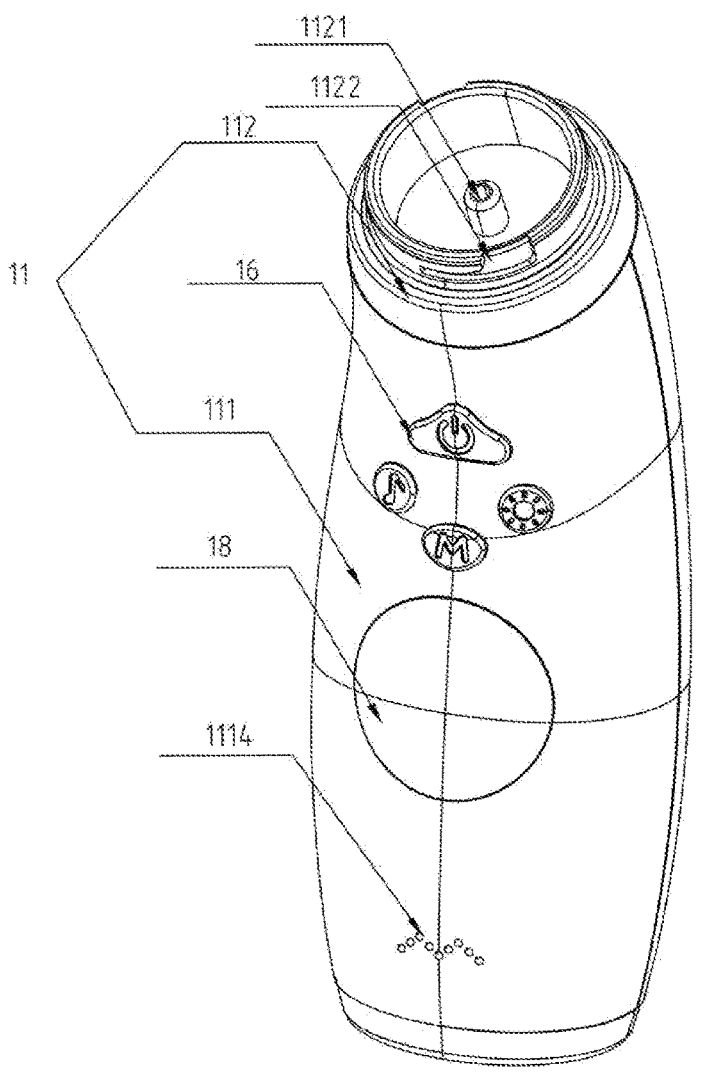
Figure 4:
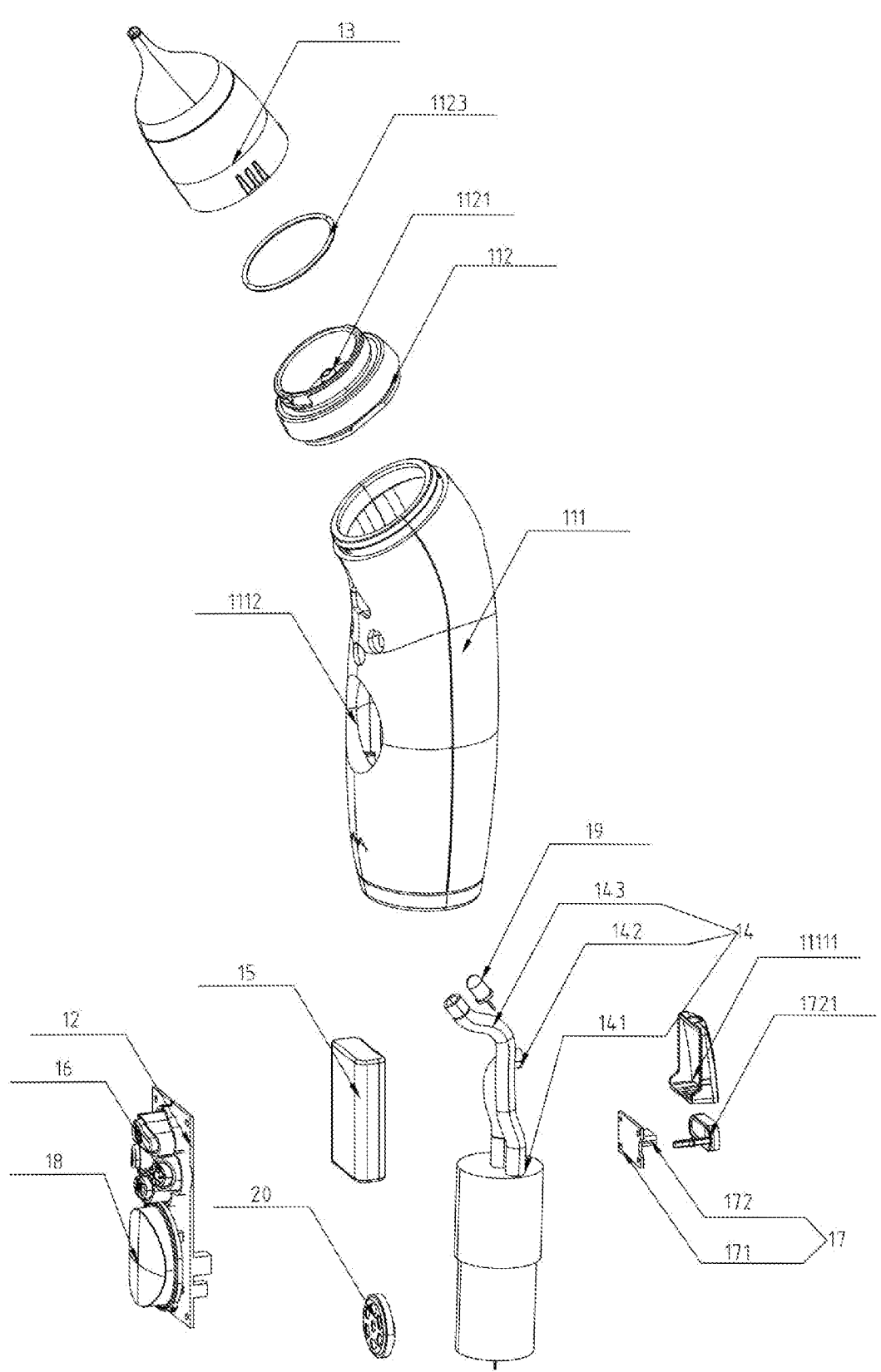
FIG. 4 is a schematic diagram of an exploded structure of the electric nasal aspirator with the anti-blocking and cleaning functions shown in FIG. 1 according to the present disclosure.
Figure 5:
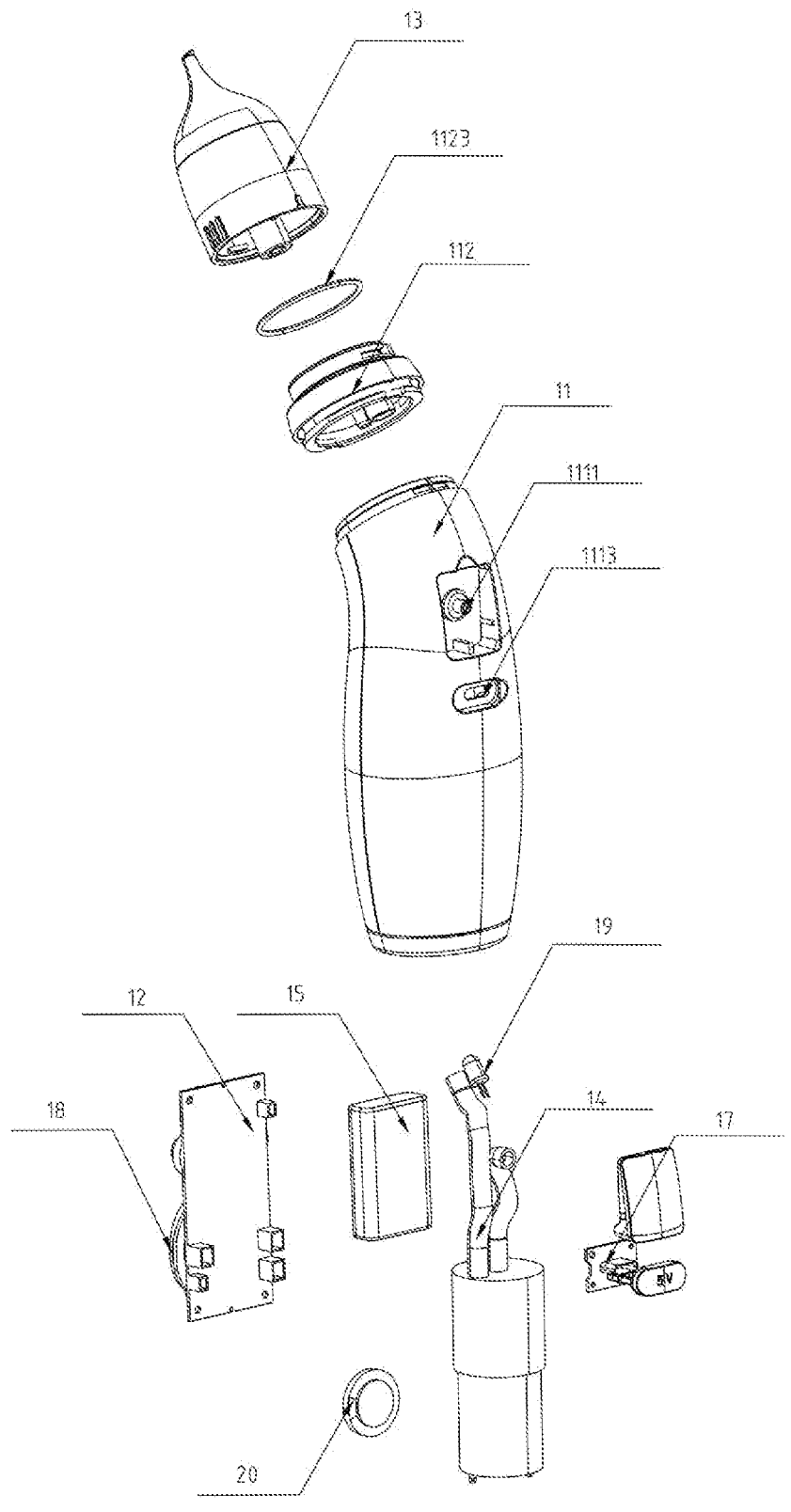
FIG. 5 is a schematic diagram of an exploded structure of the electric nasal aspirator with the anti-blocking and cleaning functions shown in FIG. 4 in another viewing angle according to the present disclosure, which includes a collection cup assembly.

Referring to FIG. 3 to FIG. 5, in this embodiment, the main housing 111 is provided with an exhaust hole 1111, a plurality of first through holes 1112, a charging interface 1113, and a plurality of speaker holes 1114 penetrating through the main housing. The exhaust hole 1111 is hermetically communicated to an exhaust end of the air pump assembly 14. The button assembly 16 and the display assembly 18 respectively penetrate through the housing assembly 11 through the corresponding first through holes 1112. Positions of the plurality of speaker holes 1114 correspond to a position of the speaker 20. In this embodiment, the cup holder 112 is provided with an air suction column 1121 penetrating through the cup holder. The air suction column 1121 is hermetically communicated to an air suction end of the air pump assembly 14. At least one clamping slot 1122 is arranged on an outer side of the cup holder 112. The collection cup assembly 13 is detachably connected to the cup holder 112 through the at least one clamping slot 1122. Meanwhile, in order to improve the sealing performance of both the collection cup assembly 13 and the cup holder 112, a sealing ring 1123 is arranged at a joint between the collection cup assembly 13 and the cup holder 112. Specifically, a material of the sealing ring 1123 is rubber or silica gel. In this embodiment, the exhaust hole 1111 is movably provided with an exhaust cover 11111. A material of the cup holder 112 is transparent or semi-transparent, so that light emitted by the LED lamp 19 arranged in the main housing 111 is transmitted out.

Referring to FIG. 3 to FIG. 5, in this embodiment, the circuit board 12 is electrically connected to the air pump assembly 14, the battery assembly 15, the button assembly 16, the charging assembly 17, the display assembly 18, the LED lamp 19, and the speaker 20, respectively. Control technologies used are all existing technologies, so specific control processes and specific models used will not be elaborated here, as long as they meet the requirements of the present disclosure.

Figure 6:
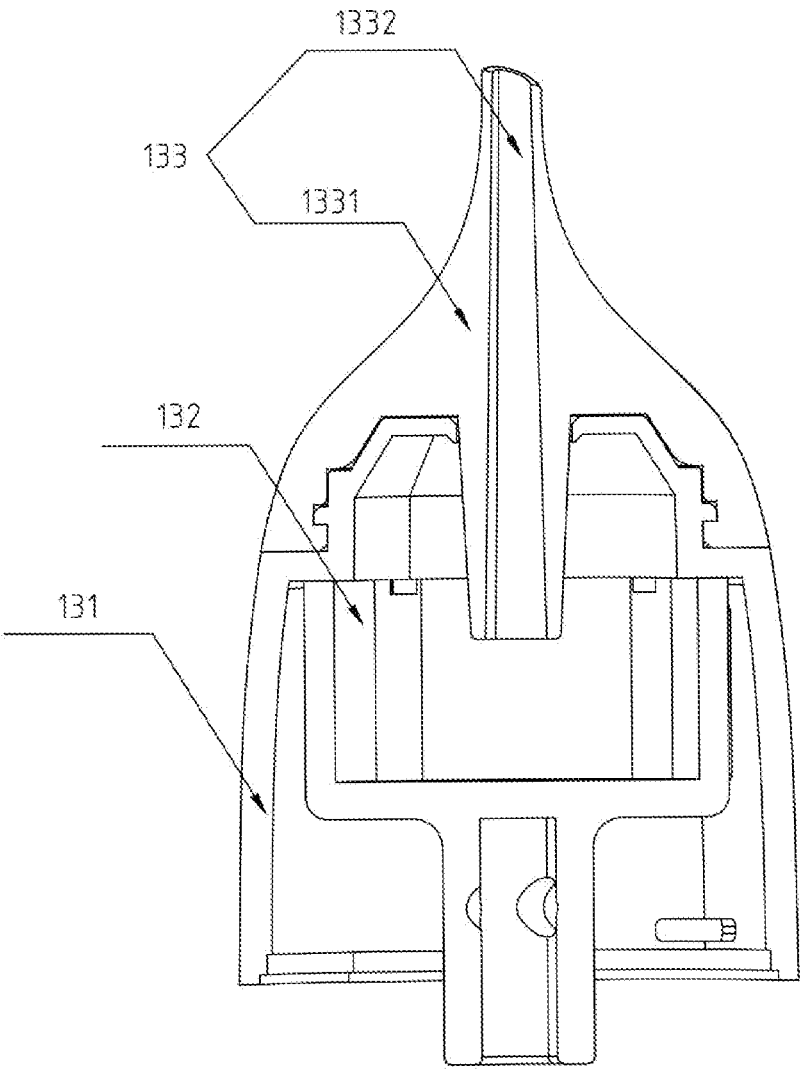
FIG. 6 is a structural sectional view of the collection cup assembly shown in FIG. 5.
Figure 7:
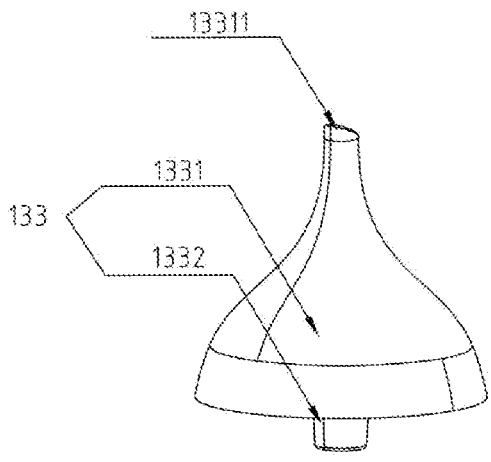
FIG. 7 is a schematic diagram of an exploded structure of the collection cup assembly shown in FIG. 5, which includes an outer cover, a collection cup, and a suction nozzle.
Figure 7:
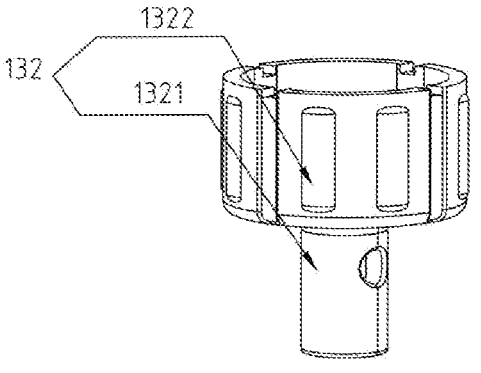
Figure 7:
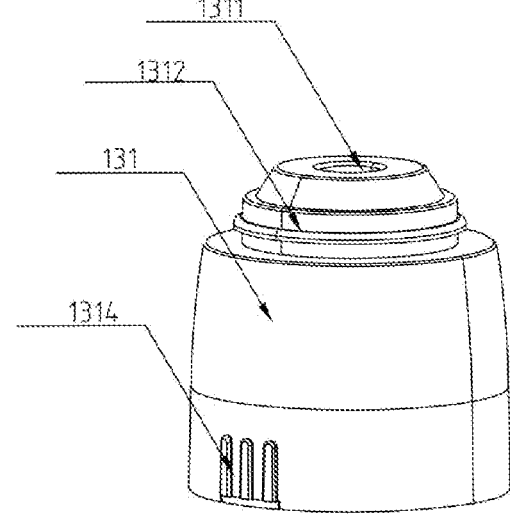

Referring to FIG. 6 and FIG. 7, in this embodiment, the collection cup assembly 13 includes an outer cover 131, a collection cup 132, and a suction nozzle 133. The outer cover 131 is detachably hermetically communicated to the housing assembly 11. The collection cup 132 is movably arranged in the outer cover 131, closely abuts against an inner wall of the outer cover 131, and can be detachably arranged on the air suction column 1121 and communicated to the air suction column 1121. The suction nozzle 133 is detachably connected to the outer cover 131 and extends into the collection cup 132, so that the nasal mucus is directly collected and stored in the collection cup 132 through the suction nozzle 133.

Figure 8:
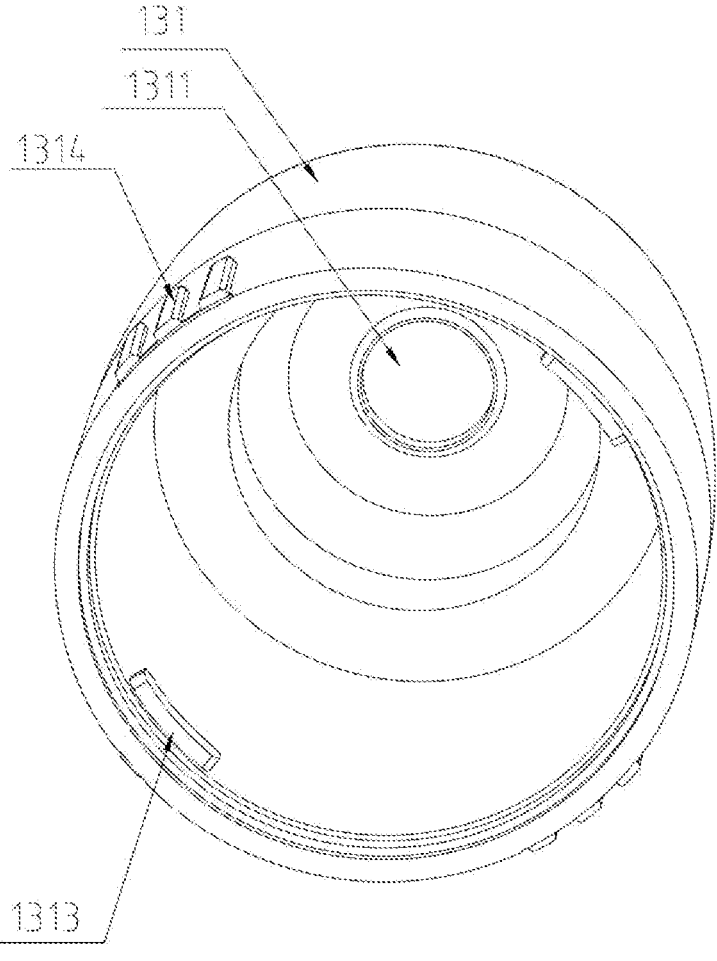
FIG. 8 is a schematic structural diagram of the outer cover shown in FIG. 7.

Referring to FIG. 6 to FIG. 8, in this embodiment, the outer cover 131 is provided with a second through hole 1311 penetrating through the outer cover, and the suction nozzle 133 penetrates through the outer cover 131 through the second through hole 1311 and extends into the collection cup 132. The outer cover 131 is provided with an external thread 1312 and a plurality of cover twisting members 1314. The suction nozzle 133 is in detachably threaded connection to the outer cover 131 through the external thread 1312. A friction force between a hand of a user and the outer cover 131 is increased by the plurality of cover twisting members 1314, so that it is convenient to detachably connect the outer cover 131 to the housing assembly 11. Specifically, the cover twisting members 1314 can be convex points or stripes. At least one buckle 1313 is arranged on an inner wall of a lower end of the outer cover 131; and the at least one buckle 1313 is matched with the corresponding clamping slot 1122, so that the outer cover 131 is detachably clamped on the housing assembly 11. In this embodiment, two buckles 1313 are fixedly arranged on the inner wall of the outer cover 131 and are respectively matched with the corresponding clamping slots 1122 to fixedly arrange the outer cover 131 on the housing assembly 11. In some embodiments, at least one clamping slot 1122 can also be arranged on an inner wall of a lower end of the outer cover 131. The outer cover 131 is fixedly arranged on the housing assembly 11 by matching the clamping slot 1122 with the corresponding buckle 1313 on the housing assembly 11. In some other embodiments, a quantity of the buckles 1313 and a quantity of the clamping slots 1122 may be one, three, or another number. The quantities are set according to an actual need, and their quantities and positions match each other. In this embodiment, the outer cover 131 adopts a transparent material, which facilitates a user to observe a condition inside the outer cover 131 in real time, and facilitates the light of the LED lamp 19 to be transmitted out of the housing assembly 11 and the outer cover 131 in sequence.

Figure 9:
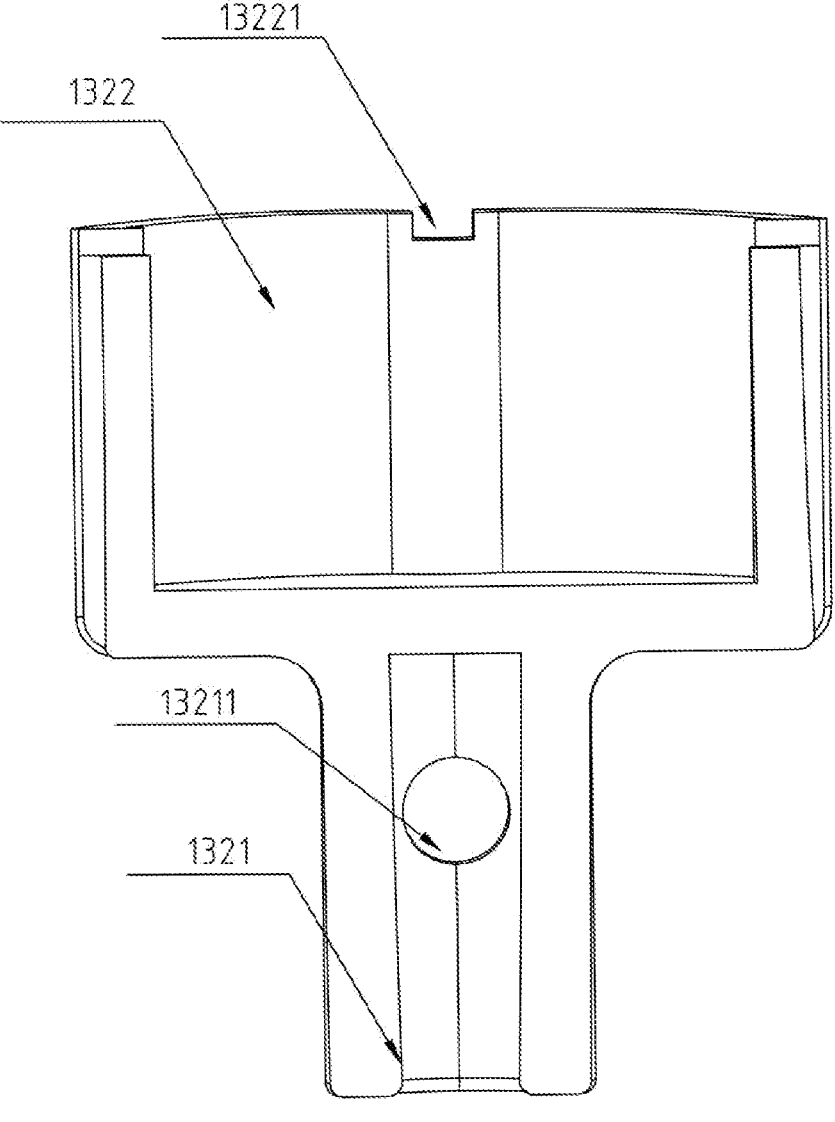
FIG. 9 is a structural sectional view of the collection cup shown in FIG. 7.

Referring to FIG. 6, FIG. 7, and FIG. 9, the collection cup 132 includes a connecting column 1321 and a collection chamber 1322; the connecting column 1321 is hollowly tubular and detachably arranged on the air suction column 1121; an upper end of the connecting column 1321 is provided with at least one air suction hole 13211 penetrating through the upper end; the air suction column 1121 is communicated to a hollow chamber encircled by the outer cover 131 and the cup holder 112 through the at least one air suction hole 13211; the collection chamber 1322 is fixedly arranged on the connecting column 1321 and can closely abut against an inner wall of the outer cover 131; at least one air suction slot body 13221 penetrating through a side edge of the collection chamber is arranged on the side edge; and the outer cover 131 is communicated to the suction nozzle 133 through the at least one air suction slot body 13221. Thus, the suction nozzle 133, the collection chamber 1322, the at least one air suction slot body 13221, the hollow chamber encircled by the outer cover 131 and the cup holder 112, the at least one air suction hole 13211, the connecting column 1321, the air suction column 1121, the air pump assembly 14, and the exhaust hole 1111 are communicated in sequence to form an air suction channel. In this embodiment, two air suction holes 13211 are respectively arranged on the connecting column 1321 in a penetrating manner. In other embodiments, a quantity of the air suction hole 13211 may be one, three, or another number, and is set according to an actual need. In this embodiment, four air suction slot bodies 13221 are respectively arranged on the side edge of the collection chamber 1322 in a penetrating manner. In other embodiments, a quantity of the air suction slot bodies 13221 may be one, two, three, or another number, and is set according to an actual need. In this embodiment, the connecting column 1321 and the collection chamber 1322 are integrally formed are both made of silica gel, which facilitates the collection chamber 1322 to closely abut against the inner wall of the outer cover 131. Preferably, a material of the connecting column 1321 and a material of the collection chamber 1322 are food grade silica gel. In other embodiments, the connecting column 1321 and the collection chamber 1322 can also be assembled.

Figure 10:
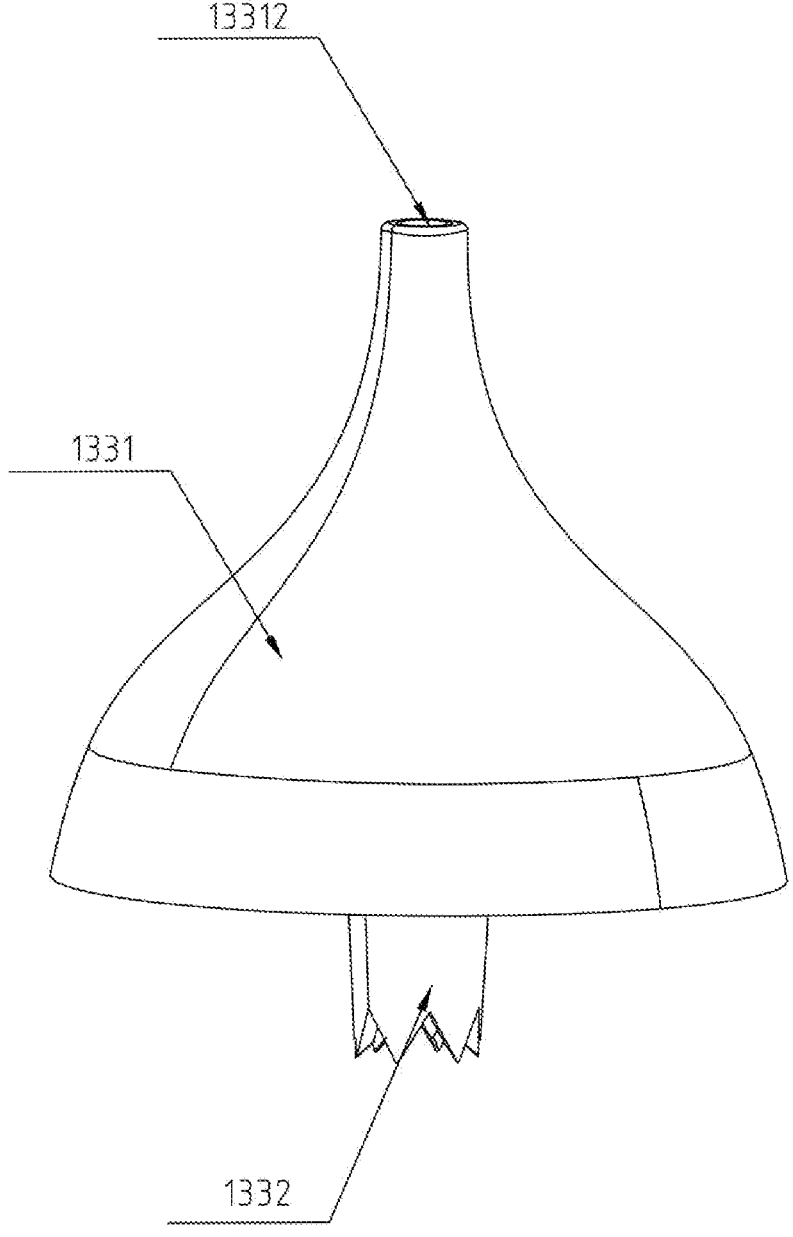
FIG. 10 is a schematic structural diagram of a second embodiment of the suction nozzle shown in FIG. 7.
Figure 11:
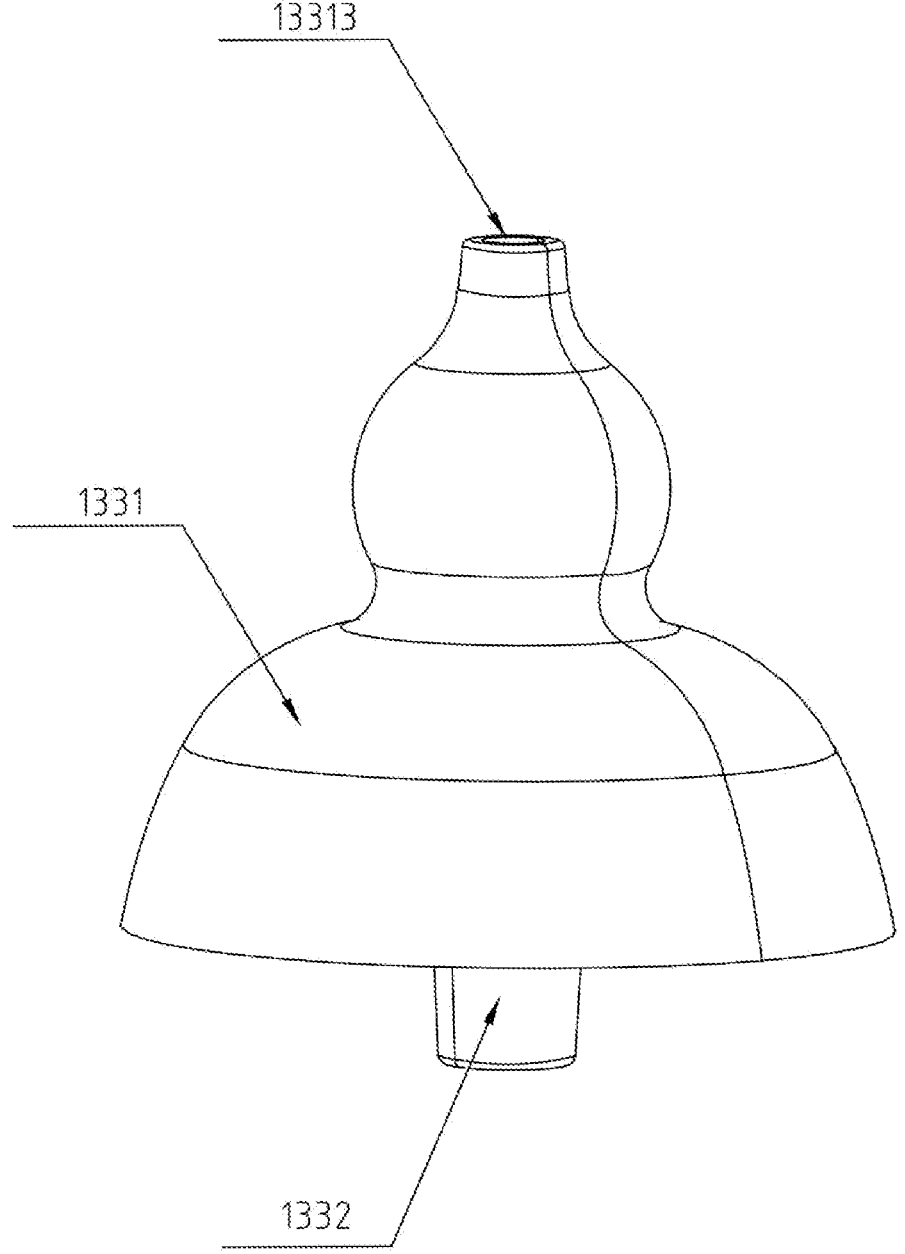
FIG. 11 is a schematic structural diagram of a third embodiment of the suction nozzle shown in FIG. 7.

Referring to FIG. 7, FIG. 10, and FIG. 11, in this embodiment, the suction nozzle 133 includes a suction nozzle main body 1331 and a suction nozzle channel 1332. An inner wall of the suction nozzle main body 1331 is provided with an internal thread; and the suction nozzle main body 1331 is in detachably threaded connection to the outer cover 131 through cooperation between the internal thread and the external thread 1312. The suction nozzle channel 1332 is arranged in the suction nozzle main body 1331 in a penetrating manner and extends into the collection chamber 1322. Specifically, a funnel-shaped incision suction nozzle port 13311, a straight head suction nozzle port 13312, or a round head suction nozzle port 13313 is arranged at a front end of the suction nozzle 133, and the corresponding suction nozzle ports can be adapted according to different needs. The funnel-shaped incision suction nozzle port 13311 is suitable for sucking the nasal mucus on inner walls of the nasal cavities of children; the straight head suction nozzle port 13312 is suitable for being used by children at the age of three or more; and the round head suction nozzle port 13313 is suitable for being used by babies under the age of three. In this embodiment, a material of the suction nozzle 133 is food grade silica gel.

Referring to FIG. 3 to FIG. 5, in this embodiment, the air pump assembly 14 includes an air pump main body 141, an exhaust pipe 142, and an air suction pipe 143. The air pump main body 141 is arranged in the housing assembly 11. One end of the exhaust pipe 142 is hermetically communicated to an exhaust end of the air pump main body 141, and the other end is hermetically communicated to the exhaust hole 1111. One end of the air suction pipe 143 is hermetically communicated to an air suction end of the air pump main body 141, and the other end is hermetically communicated to the air suction column 1121. Thus, cleaning water that enters the air pump main body 141 through the air suction column 1121 can clean the interior of the air pump main body 141 and is then discharged from the exhaust hole 1111, without entering the housing assembly 11, thus effectively preventing damage to components arranged inside the housing assembly 11.

Referring to FIG. 3 to FIG. 5, in this embodiment, the battery assembly 15 uses a polymer lithium-ion battery. In other embodiments, the battery assembly 15 can also use a dry battery or an ordinary lithium battery. In this embodiment, the button assembly 16 includes an on/off button, an audio button, a light button, and a function setting button; and the nasal aspirator is switched on or off through the on/off button. The speaker 20 and the LED lamp 19 are controlled to work respectively through the audio button and the light button; and functions are switched and set through the function setting button.

Referring to FIG. 3 to FIG. 5, in this embodiment, the charging assembly 17 includes a connecting circuit board 171 and a charging interface 172; the connecting circuit board 171 is fixedly arranged in the housing assembly 11 and electrically connected to the circuit board 12; the charging interface 172 is fixedly arranged on the connecting circuit board 171 and penetrates through the housing assembly 11; and the battery assembly 15 is charged through the charging interface 172. The charging interface 172 can use a Micro USB interface, a Type-C interface, or a Lightning interface. Preferably, the charging interface 172 adopts the Type-C interface. In order to prevent foreign matters from entering the charging interface 172, a protective plug 1721 is movably arranged on the charging interface 172.

Referring to FIG. 3 to FIG. 5, the display assembly 18 can use a digital tube, an LCD display screen, or an LED display screen. Preferably, the display assembly 18 uses a touch-control LED display screen, and functions can be set by touching the display assembly 18. In this embodiment, the LED lamp 19 can be changed in multiple colors and can flicker to create different atmospheres to attract the attention of the child and relieve the discomfort in the nasal mucus process of the child.

It should be noted that a specific working process of an electric nasal aspirator with the anti-blocking and cleaning functions of the present disclosure is as follows: The air pump assembly 14 starts air suction, and a generated negative pressure passes through the air suction pipe 143, the air suction column 1121, the connecting column 1321, the air suction hole 13211, the outer cover 131, the air suction slot body 13221, the collection chamber 1322, and the suction nozzle 133 in sequence to form an air suction channel to suck the nasal mucus in the nasal cavity of a user into the collection chamber 1322. Due to the close abutment between the collection chamber 1322 and the inner wall of the outer cover 131, it is difficult for the nasal mucus collected in the collection chamber 1322 to flow into the sealed chamber formed by the outer cover 131 and the cup holder 112. The nasal mucus in the collection chamber 1322 will overflow into the sealed chamber formed by the outer cover 131 and the cup holder 112 if the amount of the nasal mucus exceeds a capacity of the collection chamber, and the air suction hole 13211 on the connecting column 1321 will guide a source air hole that generating a negative pressure to a middle position of the connecting column 1321. This design makes it also difficult for the nasal mucus that overflows into the sealed chamber formed by the outer cover 131 and the cup holder 112 to enter the housing assembly 11 through the air suction column 1121. Due to the detachable connection between the outer cover 131, the collection cup

132, and the suction nozzle 133, the outer cover, the collection cup, and the suction nozzle are convenient to clean and disinfect. When the air pump main body 141 needs to be cleaned, cleaning water enters the air pump main body 141 through the air suction column 1121 to clean the interior of the air pump main body 141 and then is discharged from the exhaust hole 1111. As the air pump assembly 14 is hermetically communicated to the exhaust hole 1111 and the air suction column 1121, the cleaning water will not enter the housing assembly 11, thereby effectively preventing damage to components arranged inside the housing assembly 11.

The various technical features in the foregoing embodiments may be randomly combined. For concise description, not all possible combinations of the various technical features in the above embodiments are described. However, provided that combinations of these technical features do not conflict with each other, the combinations of the various technical features are considered as falling within the scope of this specification.

The foregoing embodiments merely express several implementations of the present disclosure. The descriptions thereof are relatively specific and detailed, but are not understood as limitations on the scope of the present disclosure. It should be pointed out that a person of ordinary skill in the art can also make several transformations and improvements without departing from the idea of the present disclosure. These transformations and improvements fall within the protection scope of the present disclosure. Therefore, the protection scope of the patent of the present disclosure shall be subject to the appended claims.

What is claimed is:

1. An electric nasal aspirator with anti-blocking and cleaning functions, comprising a housing assembly, which is a hollow chamber, wherein the housing assembly is provided with an exhaust hole and an air suction column penetrating through the housing assembly;

a circuit board, fixedly arranged in the housing assembly;

a collection cup assembly, detachably arranged on the housing assembly, wherein the collection cup assembly comprises an outer cover, a collection cup, and a suction nozzle; the outer cover is detachably hermetically connected to the housing assembly; the collection cup comprises a connecting column and a collection chamber; the connecting column is hollowly tubular and detachably arranged on the air suction column; an upper end of the connecting column is provided with at least one air suction hole penetrating through the upper end; the air suction column is communicated to a hollow chamber encircled by the outer cover and the housing assembly; the collection chamber is fixedly arranged on the connecting column and closely abuts against an inner wall of the outer cover; at least one air suction slot body penetrating through a side edge of the collection chamber is arranged on the side edge, and the outer cover is communicated to the suction nozzle through the at least one air suction slot body; the suction nozzle is detachably connected to the outer cover and extends into the collection cup; the nasal mucus is directly collected and stored in the collection cup through the suction nozzle;

an air pump assembly, configured to provide a negative pressure suction force for the collection cup assembly, wherein the air pump assembly is hermetically communicated to the air suction column and the exhaust hole and is electrically connected to the circuit board;

a button assembly, fixedly arranged on the circuit board and penetrating through the housing assembly, wherein the button assembly controls on/off and function settings of the nasal aspirator; and a battery assembly, fixedly arranged in the housing assembly and configured to provide electric energy for the circuit board, the air pump assembly, and the button assembly.

2. The electric nasal aspirator with the anti-blocking and cleaning functions according to claim 1, wherein the air pump assembly comprises an air pump main body, an exhaust pipe, and an air suction pipe; the air pump main body is arranged in the housing assembly; two ends of the exhaust pipe are respectively hermetically communicated with an exhaust end of the air pump main body and the exhaust hole; and two ends of the air suction pipe are respectively hermetically communicated with an air suction end of the air pump main body and the air suction column.

3. The electric nasal aspirator with the anti-blocking and cleaning functions according to claim 2, wherein the housing assembly comprises a main housing and a cup holder; the main housing is a hollow chamber with a slope; the cup holder is fixedly arranged on the main housing; and a joint between the main housing and the cup holder is welded ultrasonically to improve the waterproof performance of both the main housing and the cup holder.

4. The electric nasal aspirator with the anti-blocking and cleaning functions according to claim 3, wherein at least one clamping slot is arranged on an outer side of the cup holder; at least one buckle is arranged on the inner wall of the outer cover; and the at least one buckle is matched with the corresponding clamping slot, so that the outer cover is detachably and fixedly connected to the cup holder.

5. The electric nasal aspirator with the anti-blocking and cleaning functions according to claim 4, wherein a sealing ring is arranged at a joint between the outer cover and the cup holder; and the sealing ring improves the sealing performance of both the outer cover and the cup holder.

6. The electric nasal aspirator with the anti-blocking and cleaning functions according to claim 1, wherein the outer cover is provided with an external thread; an inner wall of the suction nozzle is provided with an internal thread; and the suction nozzle is in detachably threaded connection to the outer cover through due to cooperation between the internal thread and the external thread.

7. The electric nasal aspirator with the anti-blocking and cleaning functions according to claim 1, wherein the connecting column and the collection chamber are integrally formed, facilitating processing of the connecting column and the collection chamber; and a material of the connecting column and a material of the collection chamber are silica gel, so that the collection chamber closely abuts against the inner wall of the outer cover.

8. The electric nasal aspirator with the anti-blocking and cleaning functions according to claim 1, wherein the suction nozzle comprises a suction nozzle main body and a suction nozzle channel; the suction nozzle main body is in detachably threaded connection to the outer cover; a front end of the suction nozzle main body is provided with a suction nozzle port penetrating through the front end; and the suction nozzle channel is arranged in the suction nozzle main body in a penetrating manner and extends into the collection chamber.

9. The electric nasal aspirator with the anti-blocking and cleaning functions according to claim 8, wherein the suction nozzle port is a funnel-shaped incision suction nozzle port, a straight head suction nozzle port, or a round head suction nozzle port, and the corresponding suction nozzle port is adapted according to an actual need.

10. The electric nasal aspirator with the anti-blocking and cleaning functions according to claim 8, wherein a material of the suction nozzle is food grade silica gel.

11. The electric nasal aspirator with the anti-blocking and cleaning functions according to claim 1, wherein when the battery assembly is a rechargeable battery, a charging assembly is arranged in the housing assembly; and the charging assembly penetrates through the housing assembly and is electrically connected to the circuit board.

12. The electric nasal aspirator with the anti-blocking and cleaning functions according to claim 11, wherein the charging assembly comprises a connecting circuit board and a charging interface; the connecting circuit board is fixedly arranged in the housing assembly and electrically connected to the circuit board; the charging interface is fixedly arranged on the connecting circuit board and penetrates through the housing assembly; the battery assembly is charged through the charging interface; the charging interface is movably provided with a protective plug; and the protective plug prevents foreign matters from entering the charging interface.

13. The electric nasal aspirator with the anti-blocking and cleaning functions according to claim 12, wherein the charging interface adopts a Micro USB interface, a Type-C interface, or a Lightning interface.

14. The electric nasal aspirator with the anti-blocking and cleaning functions according to claim 1, further comprising a display assembly, wherein the display assembly is fixedly arranged on the circuit board and penetrates through the housing assembly and is configured to perform real-time displaying; and the display assembly adopts a digital tube, a liquid crystal display (LCD) screen, or a light-emitting diode (LED) display screen.

15. The electric nasal aspirator with the anti-blocking and cleaning functions according to claim 1, further comprising an LED lamp and a speaker, wherein the LED lamp and the speaker are respectively fixedly arranged in the housing assembly; light emitted by the LED lamp is transmitted out of the housing assembly and the collection cup assembly in sequence to attract attention of a child through the LED lamp and the speaker and relieve discomfort in a nasal mucus process of the child.

16. The electric nasal aspirator with the anti-blocking and cleaning functions according to claim 15, wherein the button assembly comprises an on/off button, an audio button, a light button, and a function setting button; the nasal aspirator is switched on or off through the on/off button; the speaker and the LED lamp are controlled to work respectively through the audio button and the light button; and functions are switched and set through the function setting button.

17. The electric nasal aspirator with the anti-blocking and cleaning functions according to claim 15, wherein the LED lamp is changed in multiple colors and flickers to create different atmospheres to attract the attention of the child and relieve the discomfort in the nasal mucus process of the child.

\* \* \* \* \*